(12) United States Patent
Raghunathan

(10) Patent No.: US 8,748,356 B2
(45) Date of Patent: Jun. 10, 2014

(54) METHODS FOR USE IN HUMAN-ADAPTING MONOCLONAL ANTIBODIES

(75) Inventor: Gopalan Raghunathan, San Diego, CA (US)

(73) Assignee: Janssen Biotech, Inc., Horsham, PA (US)

(*) Notice: Subject to any disclaimer, the term of this patent is extended or adjusted under 35 U.S.C. 154(b) by 1241 days.

(21) Appl. No.: 11/875,416

(22) Filed: Oct. 19, 2007

(65) Prior Publication Data

US 2009/0118127 A1     May 7, 2009

(51) Int. Cl.
| | |
|---|---|
| *C40B 50/06* | (2006.01) |
| *C40B 40/10* | (2006.01) |
| *C12P 21/08* | (2006.01) |
| *A61K 39/395* | (2006.01) |

(52) U.S. Cl.
USPC .......... 506/26; 424/133.1; 530/387.3; 506/18

(58) Field of Classification Search
USPC ................ 506/18, 26; 530/387.3; 424/133.1
See application file for complete search history.

(56) References Cited

U.S. PATENT DOCUMENTS

| | | | | |
|---|---|---|---|---|
| 5,565,332 | A * | 10/1996 | Hoogenboom et al. | ...... 435/69.1 |
| 6,696,248 | B1 * | 2/2004 | Knappik et al. | .................. 435/6 |
| 2009/0238825 | A1 | 9/2009 | Kovacevich et al. | |

FOREIGN PATENT DOCUMENTS

| | | | | |
|---|---|---|---|---|
| WO | WO 2004/006955 | * | 1/2004 | ........... A61K 39/395 |
| WO | WO 2004/006955 A1 | | 1/2004 | |
| WO | WO 2005/079479 A2 | | 9/2005 | |
| WO | WO 2005/112564 | * | 12/2005 | ............. C07K 16/30 |
| WO | WO 2005/112564 A2 | | 12/2005 | |

OTHER PUBLICATIONS

Co, et al., "A Humanized Antibody Specific for the Platelet Integrin gpIIb/IIIa," Journal of Immunology, 152: 2968-2976 (1994).
Dall'Acqua, et al., "Antibody humanization by framework shuffling," Methods, 36: 43-60 (2005).
Gonzales, et al., "Minimizing immunogenicity of the SDR-grafted humanized antibody CC49 by generic manipulation of the framework residues," Molecular Immunology, 40: 337-349 (2003).
Gorman, et al., "Reshaping a therapeutic CD4 antibody," Proceedings of the National Academy of Science USA, 88 4181-4185 (1991).
Hwang, et al., "Use of human germline genes in a CDR homology-based approach to antibody humanization," Methods, 36: 35-42 (2005).
Jones, et al., "Replacing the complementarity-determining regions in a human antibody with those from a mouse," Nature, 321: 522-525 (1986).
Kashmiri, et al., "SDR grafting—a new approach to antibody humanization," Methods, 36: 25-34 (2005).
Queen, et al., "A humanized antibody that binds to the interleukin 2 receptor," Proceedings of the National Academy of Science USA, 86: 10029-10033 (1989).
Sali, et al., "Comparative Protein Modelling by Satisfaction of Spatial Restraints," Journal of Molecular Biology, 234: 779-815 (1993).
Tan, et al., ""Superhumanized" Antibodies: Reduction of Immunogenic potential by Complementarity-Determining Region Grafting with Human Germline Sequences: Application to an Anti-CD28," Journal of Immunology, 169: 1119-1125 (2002).
Tempest, et al., "Reshaping a Human Monoclonal Antibody to Inhibit Human Respiratory Syncytial Virus Infection In Vivo," Bio/Technology, 9: 266-271 (1991).
European Search Report dated Mar. 4, 2009.

* cited by examiner

*Primary Examiner* — Amber D Steele
(74) *Attorney, Agent, or Firm* — Kirk Baumeister

(57) ABSTRACT

Methods useful for human adapting non-human monoclonal antibodies are disclosed. The methods select candidate human antibody framework sequences from a database of human germline genes or human sequences with somatic mutations.

4 Claims, 11 Drawing Sheets

Fig. 5

FR1
C7         EVQLVESGGGLVQPGGSLRLSCAAS        (SEQ ID NO: 5)
Infliximab --K-E-----------MK---V--

FR2
C7         WVRQAPGKGLEWIG (SEQ ID NO: 6)
Infliximab ----S-E-----VA

FR3
C7         RFIISRDDNKNSLYLEMNSLKTEDTAEYYCAR (SEQ ID NO: 7)
Infliximab --T-----S-SAV---Q--TD-R----GV---S-

FR4
C7         WGQGTLVTVS (SEQ ID NO: 8)
Infliximab -----TL---

Fig. 6

FR1
C7          EIVLTQSPDFQSVTPKEKVTITC (SEQ ID NO: 9)
Infliximab  D-L-----AIL---S-G-RVSFS-

FR2
C7          WYQQKPDQSPKLLIK (SEQ ID NO: 10)
Infliximab  ----RTNG---R----

FR3
C7          GVPSRFSGSGSGTDFTFTISSLEAEDAATYYC (SEQ ID NO: 11)
Infliximab  -I-------------LS-NTV-S---I-D---

FR4
C7          FGPGTKVDIK (SEQ ID NO: 12)
Infliximab  --S---NLEV-

Fig. 8

FR1
B21M          QITLKESGPTLVKPTQTLTLTCTFS (SEQ ID NO: 13)
Murine F101   -V-------GILQ-S---S---S--

FR2
B21M          WIRQPPGKALEWLA (SEQ ID NO: 14)
Murine F101   -----S--G-----

FR3
B21M          RLTITKDTSKNQVVLTMTNMDPVDTATYYCAR(SEQ ID NO: 15)
Murine F101   ----S----R---F-KI-SV-TA---------

FR4
B21M          WGQGTLVTVSS (SEQ ID NO: 16)
Murine F101   ----------A

Fig. 9

FR1
B21M............DIVMTQSPDSLAVSLGERATINC (SEQ ID NO: 17)
Murine F101.....---L----A-------Q----F-

FR2
B21M............WYQQKPGQPPKLLIY (SEQ ID NO: 18)
Murine F101.....-F-------------

FR3
B21M............GVPDRFSGSGSGTDFTLTISSLQAEDVAVYYC (SEQ ID NO: 19)
Murine F101.....-I-A--T---------NIHPVEE--A-T---

FR4
B21M............FGQGTKVEIK (SEQ ID NO: 20)
Murine F101.....--G-------

SEQUENCE LISTING

```
<160> NUMBER OF SEQ ID NOS: 20

<210> SEQ ID NO 1
<211> LENGTH: 119
<212> TYPE: PRT
<213> ORGANISM: Artificial Sequence
<220> FEATURE:
<223> OTHER INFORMATION: Infliximab VH

<400> SEQUENCE: 1

Glu Val Lys Leu Glu Glu Ser Gly Gly Gly Leu Val Gln Pro Gly Gly
 1               5                  10                  15

Ser Met Lys Leu Ser Cys Val Ala Ser Gly Phe Ile Phe Ser Asn His
            20                  25                  30

Trp Met Asn Trp Val Arg Gln Ser Pro Glu Lys Gly Leu Glu Trp Val
        35                  40                  45

Ala Glu Ile Arg Ser Lys Ser Ile Asn Ser Ala Thr His Tyr Ala Glu
    50                  55                  60

Ser Val Lys Gly Arg Phe Thr Ile Ser Arg Asp Asp Ser Lys Ser Ala
65                  70                  75                  80

Val Tyr Leu Gln Met Thr Asp Leu Arg Thr Glu Asp Thr Gly Val Tyr
                85                  90                  95

Tyr Cys Ser Arg Asn Tyr Tyr Gly Ser Thr Tyr Asp Tyr Trp Gly Gln
            100                 105                 110

Gly Thr Thr Leu Thr Val Ser
        115

<210> SEQ ID NO 2
<211> LENGTH: 107
<212> TYPE: PRT
<213> ORGANISM: Artificial Sequence
```

-continued

```
<220> FEATURE:
<223> OTHER INFORMATION: Infliximab VL

<400> SEQUENCE: 2

Asp Ile Leu Leu Thr Gln Ser Pro Ala Ile Leu Ser Val Ser Pro Gly
 1               5                  10                  15

Glu Arg Val Ser Phe Ser Cys Arg Ala Ser Gln Phe Val Gly Ser Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Met Ser Gly Ile Pro Ser Arg Phe Ser Gly
50                  55                  60

Ser Gly Ser Gly Thr Asp Phe Thr Leu Ser Ile Asn Thr Val Glu Ser
65                  70                  75                  80

Glu Asp Ile Ala Asp Tyr Tyr Cys Gln Gln Ser His Ser Trp Pro Phe
                85                  90                  95

Thr Phe Gly Ser Gly Thr Asn Leu Glu Val Lys
            100                 105

<210> SEQ ID NO 3
<211> LENGTH: 120
<212> TYPE: PRT
<213> ORGANISM: Mus musculus

<400> SEQUENCE: 3

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
                20                  25                  30

Gly Met Gly Val Ser Trp Ile Arg Gln Pro Ser Gly Lys Gly Leu Glu
            35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95

Cys Ala Arg Leu Tyr Gly Phe Thr Tyr Gly Phe Ala Tyr Trp Gly Gln
            100                 105                 110

Gly Thr Leu Val Thr Val Ser Ala
        115                 120

<210> SEQ ID NO 4
<211> LENGTH: 112
<212> TYPE: PRT
<213> ORGANISM: Mus musculus

<400> SEQUENCE: 4

Asp Ile Val Leu Thr Gln Ser Pro Ala Ser Leu Ala Val Ser Leu Gly
 1               5                  10                  15

Gln Arg Ala Thr Ile Phe Cys Arg Ala Ser Gln Ser Val Asp Tyr Asn
                20                  25                  30

Gly Ile Ser Tyr Met His Trp Phe Gln Gln Lys Pro Gly Gln Pro Pro
            35                  40                  45

Lys Leu Leu Ile Tyr Ala Ala Ser Asn Pro Glu Ser Gly Ile Pro Ala
50                  55                  60

Arg Phe Thr Gly Ser Gly Ser Gly Thr Asp Phe Thr Leu Asn Ile His
65                  70                  75                  80
```

```
Pro Val Glu Glu Glu Asp Ala Ala Thr Tyr Tyr Cys Gln Gln Ile Ile
                85                  90                  95

Glu Asp Pro Trp Thr Phe Gly Gly Gly Thr Lys Leu Glu Ile Lys Arg
            100                 105                 110

<210> SEQ ID NO 5
<211> LENGTH: 25
<212> TYPE: PRT
<213> ORGANISM: Artificial Sequence
<220> FEATURE:
<223> OTHER INFORMATION: A C7 VH FR1

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 6
<211> LENGTH: 14
<212> TYPE: PRT
<213> ORGANISM: Artificial Sequence
<220> FEATURE:
<223> OTHER INFORMATION: A C7 VH FR2

<400> SEQUENCE: 6

Trp Val Arg Gln Ala Pro Gly Lys Gly Leu Glu Trp Ile Gly
1               5                   10

<210> SEQ ID NO 7
<211> LENGTH: 32
<212> TYPE: PRT
<213> ORGANISM: Artificial Sequence
<220> FEATURE:
<223> OTHER INFORMATION: A C7 VH FR3

<400> SEQUENCE: 7

Arg Phe Ile Ile Ser Arg Asp Asp Asn Lys Asn Ser Leu Tyr Leu Glu
1               5                   10                  15

Met Asn Ser Leu Lys Thr Glu Asp Thr Ala Glu Tyr Tyr Cys Ala Arg
            20                  25                  30

<210> SEQ ID NO 8
<211> LENGTH: 10
<212> TYPE: PRT
<213> ORGANISM: Artificial Sequence
<220> FEATURE:
<223> OTHER INFORMATION: A C7 VH FR4

<400> SEQUENCE: 8

Trp Gly Gln Gly Thr Leu Val Thr Val Ser
1               5                   10

<210> SEQ ID NO 9
<211> LENGTH: 23
<212> TYPE: PRT
<213> ORGANISM: Artificial Sequence
<220> FEATURE:
<223> OTHER INFORMATION: A C7 VL FR1

<400> SEQUENCE: 9

Glu Ile Val Leu Thr Gln Ser Pro Asp Phe Gln Ser Val Thr Pro Lys
1               5                   10                  15

Glu Lys Val Thr Ile Thr Cys
            20
```

```
<210> SEQ ID NO 10
<211> LENGTH: 15
<212> TYPE: PRT
<213> ORGANISM: Artificial Sequence
<220> FEATURE:
<223> OTHER INFORMATION: A C7 VL FR2

<400> SEQUENCE: 10

Trp Tyr Gln Gln Lys Pro Asp Gln Ser Pro Lys Leu Leu Ile Lys
 1               5                  10                  15

<210> SEQ ID NO 11
<211> LENGTH: 32
<212> TYPE: PRT
<213> ORGANISM: Artificial Sequence
<220> FEATURE:
<223> OTHER INFORMATION: A C7 VL FR3

<400> SEQUENCE: 11

Gly Val Pro Ser Arg Phe Ser Gly Ser Gly Ser Gly Thr Asp Phe Thr
 1               5                  10                  15

Phe Thr Ile Ser Ser Leu Glu Ala Glu Asp Ala Ala Thr Tyr Tyr Cys
            20                  25                  30

<210> SEQ ID NO 12
<211> LENGTH: 10
<212> TYPE: PRT
<213> ORGANISM: Artificial Sequence
<220> FEATURE:
<223> OTHER INFORMATION: A C7 VL FR4

<400> SEQUENCE: 12

Phe Gly Pro Gly Thr Lys Val Asp Ile Lys
 1               5                  10

<210> SEQ ID NO 13
<211> LENGTH: 25
<212> TYPE: PRT
<213> ORGANISM: Artificial Sequence
<220> FEATURE:
<223> OTHER INFORMATION: A B21M VH FR1

<400> SEQUENCE: 13

Gln Ile Thr Leu Lys Glu Ser Gly Pro Thr Leu Val Lys Pro Thr Gln
 1               5                  10                  15

Thr Leu Thr Leu Thr Cys Thr Phe Ser
            20                  25

<210> SEQ ID NO 14
<211> LENGTH: 14
<212> TYPE: PRT
<213> ORGANISM: Artificial Sequence
<220> FEATURE:
<223> OTHER INFORMATION: A B21M VH FR2

<400> SEQUENCE: 14

Trp Ile Arg Gln Pro Pro Gly Lys Ala Leu Glu Trp Leu Ala
 1               5                  10

<210> SEQ ID NO 15
<211> LENGTH: 32
<212> TYPE: PRT
<213> ORGANISM: Artificial Sequence
<220> FEATURE:
<223> OTHER INFORMATION: A B21M VH FR3
```

-continued

```
<400> SEQUENCE: 15

Arg Leu Thr Ile Thr Lys Asp Thr Ser Lys Asn Gln Val Val Leu Thr
 1               5                  10                  15

Met Thr Asn Met Asp Pro Val Asp Thr Ala Thr Tyr Tyr Cys Ala Arg
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: A B21M VH FR4

<400> SEQUENCE: 16

Trp Gly Gln Gly Thr Leu Val Thr Val Ser Ser
 1               5                  10

<210> SEQ ID NO 17
<211> LENGTH: 23
<212> TYPE: PRT
<213> ORGANISM: Artificial Sequence
<220> FEATURE:
<223> OTHER INFORMATION: A B21M VL FR1

<400> SEQUENCE: 17

Asp Ile Val Met Thr Gln Ser Pro Asp Ser Leu Ala Val Ser Leu Gly
 1               5                  10                  15

Glu Arg Ala Thr Ile Asn Cys
            20

<210> SEQ ID NO 18
<211> LENGTH: 15
<212> TYPE: PRT
<213> ORGANISM: Artificial Sequence
<220> FEATURE:
<223> OTHER INFORMATION: A B21M VL FR2

<400> SEQUENCE: 18

Trp Tyr Gln Gln Lys Pro Gly Gln Pro Pro Lys Leu Leu Ile Tyr
 1               5                  10                  15

<210> SEQ ID NO 19
<211> LENGTH: 32
<212> TYPE: PRT
<213> ORGANISM: Artificial Sequence
<220> FEATURE:
<223> OTHER INFORMATION: A B21M VL FR3

<400> SEQUENCE: 19

Gly Val Pro Asp Arg Phe Ser Gly Ser Gly Ser Gly Thr Asp Phe Thr
 1               5                  10                  15

Leu Thr Ile Ser Ser Leu Gln Ala Glu Asp Val Ala Val Tyr Tyr Cys
            20                  25                  30

<210> SEQ ID NO 20
<211> LENGTH: 10
<212> TYPE: PRT
<213> ORGANISM: Artificial Sequence
<220> FEATURE:
<223> OTHER INFORMATION: A B21M VL FR4

<400> SEQUENCE: 20

Phe Gly Gln Gly Thr Lys Val Glu Ile Lys
 1               5                  10
```

US 8,748,356 B2

METHODS FOR USE IN HUMAN-ADAPTING MONOCLONAL ANTIBODIES

FIELD OF THE INVENTION

This invention relates to methods for selecting human variable region frameworks for use in human adaptation of non-human monoclonal antibodies such as rodent antibodies. The frameworks can be of germline or somatic origin.

BACKGROUND OF THE INVENTION

Antibody human adaptation is a generic term describing the engineering of xenogeneic monoclonal antibodies (mAbs) against human therapeutic targets to maximally replace the xenogeneic sequences with human antibody sequences while preserving their antigen-binding specificities. The aim is to reduce the immunogenicity of these antibodies to improve their therapeutic properties. The engineered antibodies generated are also known in the art as humanized or CDR-grafted antibodies.

Currently, the most widely used technique for antibody human adaptation is known as "CDR grafting." The scientific basis of this technology is that the binding specificity of an antibody resides primarily within the three hypervariable loops known as the complementarity determining regions (CDRs) of its light and heavy chain variable regions (V-regions), whereas the more conserved framework regions (framework, FW; framework region, FR) provide structure support function. By grafting the CDRs to an appropriately selected FW, some or all of the antibody-binding activity can be transferred to the resulting recombinant antibody. The first demonstration of the transfer of specificity by CDR grafting was for a hapten nitrophenol (Jones et al., Nature 321:522-525 (1986)).

Since the methodology for defining CDRs has been well established, the key to CDR grafting is the selection of a most appropriate human antibody acceptor for the graft. Various strategies have been developed to select human antibody acceptors with the highest similarities to the amino acid sequences of donor CDRs or donor FW, or to the donor structures. All these "best fit" strategies, while appearing very rational, are in fact based on one assumption, i.e., a resulting recombinant antibody that is most similar (in amino acid sequence or in structure) to the original antibody will best preserve the original antigen binding activity. While these strategies have all been successfully applied to generate therapeutic antibodies (e.g., Tempest et al., Biotechnology 9:266-71 (1991), Gorman et al., Proc. Natl. Acad. Sci. USA 88:4181-4185 (1991), Co et al., J. Immunol. 152:2968-76 (1994)), the underlying hypothesis has never been seriously tested.

One potential problem of the best-fit strategies is that the criteria of best fits are mathematical, but not necessarily biological. The fitness measured by the degree of homology, for example, is the sum of numerical values assigned to identical, homologous, and dissimilar amino acid residues or nucleic acid sequences. Although these assigned values have largely been validated in many other homology evaluating systems, the fine differences that may not be significant for other systems could be important for calculating the best fits in antibody human adaptation.

A related problem is, given two acceptors with identical or very close degree of total fitness for the donor, their local fitness in different FRs may be different. In short, a mathematical model has not yet been validated to satisfy the requirement of calculating the best fits in donor-acceptor relationship in antibody engineering.

A further complication relates to the interactions between the two chains of an antibody: a best-fit heavy chain acceptor and a best-fit light chain acceptor may not fit with each other to best conserve the binding activity of the donor. No tool is available to evaluate interchain fitness. Investigators have paired heavy and light chains of several antibodies against the same epitope to try to find a better pairing. However, this has not been attempted in antibody human adaptation.

In theory, all human germline sequences have been sequenced and are available for antibody FW searching. In practice, however, the majority of human V regions that have been used so far in antibody humanization are from mature antibody genes, often those of myeloma proteins. They are likely to contain somatic mutations. These mutations are unique to the individual from which the rearranged genes were derived, and hence will be seen as foreign by other individuals. Germline database sequences are generally more suitable for antibody humanization from this perspective. However, there are only a few dozen V genes and fewer J genes available. Hence, in some instances, it may be difficult to find a germline framework that is highly compatible with the non-human sequence. In contrast, the number of available mature human antibody gene sequences is a few orders of magnitude higher than the human germline sequences. Thus, it is highly likely that one can obtain a compatible sequence in this larger dataset.

A problem of using mature antibody genes for acceptor FW is that not all of the potential V-J combinations for light chain or V-D-J combinations for heavy chain are represented in the mature genes. Thus, situations can arise in which a closely matching V gene is linked to a poorly matching J segment. The humanization of the mouse anti-Tac monoclonal antibody described by Queen et al., (Proc. Natl. Acad. Sci. USA 86:10029-10033 (1989)) is an example. Comparison of the anti-Tac $V_H$ region to the NBRF-PIR database (http:_//www_psc_edu/general/software/packages/nbrf-pir/nbrf_html) indicated that the $V_H$ region of the human myeloma protein Eu had the highest degree of homology (57% identical over $VDJ_H$). However, framework 4 of the Eu $V_H$ region has several amino acids, presumably encoded by the Eu $J_H$ segment, that are atypical of human $J_H$ segments. This resulted in a poor match between the Eu framework 4 and that of anti-Tac. Separate comparison of the anti-Tac $J_H$ region (framework 4 and the framework 4—proximal end of CDR3) to the amino acid sequences of the known functional human $J_H$ segments (of which there are 6) indicates that human $J_H4$ is a much better-match than the Eu $J_H$. This example suggests that separate comparisons of V and J elements are more advantageous than comparison of the whole variable regions between rodent and human antibody sequences. Currently, a tool for this type of separate comparison is not readily available.

Not all amino acids in the CDRs are involved in antigen binding. Thus, it has been proposed that the grafting of only those residues that are critical in antigen-antibody interaction—the so-called specificity determining residues grafting (SDR-grafting)—will further increase the content of human antibody sequences in the resulting recombinant antibody (Kashmiri et al., Methods 36:25-34 (2005); Gonzales et al., Mol Immunol. 40:337-49 (2004)). The application of this strategy requires information on the antibody structure as well as antibody-antigen contact residues, which are quite often unavailable. Even when such information is available, there is no systematic method to reliably identify the SDRs, and SDR-grafting remains so far mostly at the basic research level.

Recently, a novel strategy called "human framework shuffling" has been developed (Dall'Acqua et al., *Methods* 36:43-60 (2005)). This technique works by ligating DNA fragments encoding CDRs to DNA fragments encoding human FR1, FR2, FR3, and FR4, thus generating a library of all combinations between donor CDRs and human FRs. While this strategy has been successfully applied, there are two potential problems. First, the FRs of the resulting antibody, while all of human sources, are likely to be from non-contiguous FWs, and therefore unnatural. It remains to be seen whether these unnatural FWs will be immunogenic in humans. Second, the library, in theory, can be prohibitively large, and places a high demand on screening and assay resources.

Thus, a need exists for improved methods for making human-adapted antibodies.

BRIEF DESCRIPTION OF THE DRAWINGS

FIG. 5 shows a comparison of VH regions between human-adapted C7 and chimeric infliximab (mouse VH). Dashes denote identical residues.

FIG. 6 shows a comparison of VL regions between human-adapted C7 and chimeric infliximab (mouse VL). Dashes denote identical residues.

FIG. 8 shows a comparison of VH regions between the human-adapted B21M and mouse anti-RSV F101 antibody. Dashes denote identical residues.

FIG. 9 shows a comparison of VL regions between the human-adapted B21M and the mouse anti-RSV F101 antibody. Dashes denote identical residues.

SUMMARY OF THE INVENTION

Figure 1:
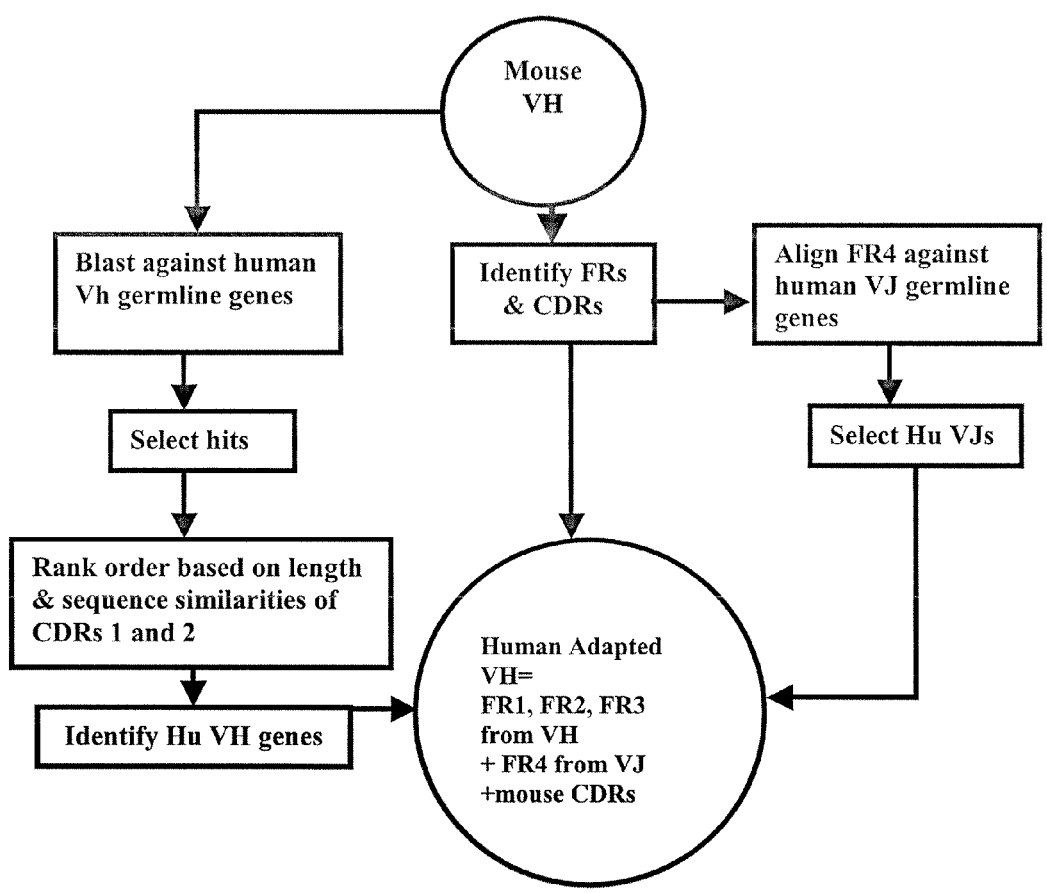
FIG. 1 shows a flowchart for the human adaptation of a mouse antibody heavy chain using a database of human germline heavy chains.

One aspect of the invention is a method for selecting human germline antibody sequences for use in making human-adapted antibody molecules comprising the steps of:
  a. obtaining a peptide sequence for a non-human antibody variable region;
  b. delineating the complementarity determining regions (CDRs) and framework regions (FRs) of the non-human antibody variable region peptide sequence;
  c. providing a library of human germline antibody gene peptide sequences comprising VH, Vκ, Vλ JH, Jκ and Jλ gene sub-libraries;
  d. selecting a subset of peptide sequences from the human germline gene library that have maximum CDR and FR similarities to the non-human antibody;
  e. selecting a subset of the human germline antibody heavy chain sequences selected in step d based on:
    e1. comparison of length compatibilities of CDR1 and CDR2 loops with the non-human antibody; and
    e2. sequence similarities of CDR1 and CDR2 loops with the non-human antibody;
  f. selecting a subset of the human germline antibody light chain sequences selected in step d based on:
    f1. comparison of length compatibilities of CDR1, CDR2 and a portion of CDR3 loops with the non-human antibody; and
    f2. sequence similarities of CDR1, CDR2 and a portion of CDR3 loops with the non-human antibody;
  g. selecting a subset of heavy chain J gene peptide sequences from the human germline JH gene sub-library based on sequence similarities between framework 4 of the non-human antibody and JH gene regions;
  h. selecting a subset of J gene peptide sequences for the light chain from the human germline Jκ and Jλ gene sub-libraries based on sequence similarities between framework 4 of the non-human antibody and Jκ and Jλ gene regions;
  i. combining a selection of FR 1, 2 and 3 from step e and a selection of FR4 from step g for human heavy chains to select human antibody heavy chain sequences for use in making human-adapted antibodies; and
  j. combining a selection of FR 1, 2 and 3 from step f and a selection of FR4 from step h for human light chains to select human antibody light chain sequences for use in making human-adapted antibodies.

Another aspect of the invention is a method for selecting human antibody sequences that contain somatic mutation for use in making human-adapted antibody molecules comprising the steps of:
  a. obtaining a peptide sequence for a non-human antibody variable region;
  b. delineating the complementarity determining regions (CDRs) and framework regions (FRs) of the non-human antibody variable region peptide sequence;
  c. providing a library of human somatic antibody gene peptide sequences;
  d. selecting a subset of peptide sequences from the human somatic gene library that have maximum CDR and FR similarities to the heavy and light chains of the non-human antibody;
  e. selecting a subset of the human somatic antibody heavy chain sequences selected in step d for use in making human-adapted antibodies based on:
    e1. comparison of length compatibilities of CDR1, CDR2 and CDR3 loops with the non-human antibody; and
    e2. sequence similarities of CDR1, CDR2 and CDR3 loops with the non-human antibody; and
  f. selecting a subset of the human somatic antibody light chain sequences selected in step d for use in making human-adapted antibodies based on:
    f1. comparison of length compatibilities of CDR1, CDR2 and CDR3 loops with the non-human antibody; and
    f2. sequence similarities of CDR1, CDR2 and CDR3 loops with the non-human antibody.

DETAILED DESCRIPTION OF THE INVENTION

All publications, including but not limited to patents and patent applications, cited in this specification are herein incorporated by reference as though fully set forth.

As used herein and in the claims, the singular forms "a," "and," and "the" include plural reference unless the context clearly dictates otherwise. Thus, for example, reference to "a human-adapted antibody" is a reference to one or more human-adapted antibodies.

Unless defined otherwise, all technical and scientific terms used herein have the same meaning as commonly understood by one of ordinary skill in the art to which this invention belongs. Although methods similar or equivalent to those described herein can be used in the practice or testing of the invention, exemplary methods are described herein.

The term "antibody" means immunoglobulin or antibody molecules and antibody fragments. In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa (κ) and lambda (λ), based on the amino acid sequences of their constant domains.

Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

Antibodies are secreted proteins constitutively expressed and secreted by plasma cells. Antibodies can also be produced using plasma cells immortalized by standard methods such as hybridoma generation or by transfection of antibody heavy and/or light chain genes into an immortalized B cell such as a myeloma cell or other cell types, such as Chinese hamster ovary (CHO) cells, plant cells and insect cells.

The term "antibody fragments" means a portion of an intact antibody, generally the antigen binding or variable region of the intact antibody. Examples of antibody fragments include Fab, Fab', $F(ab')_2$ and Fv fragments, diabodies, single chain antibody molecules, such as scFv molecules where the variable heavy and variable light chains are connected as a single polypeptide chain by a linker and multispecific antibodies formed from at least two intact antibodies.

Humanized, human-adapted and CDR-grafted antibodies are chimeric monoclonal antibodies containing CDRs from a non-human species and variable region framework regions and constant regions from a human antibody.

The present invention provides a novel structure-based human adaptation method based on molecular structures, modeling and sequences for human engineering of antibody molecules. The method results in human antibody molecules whose sequences are highly similar to human sequences (in order to reduce potential immunogenicity) and whose affinities to antigen are comparable to the parent non-human, typically mouse, antibody. The steps in the process comprise comparing a mouse sequence to a database of human sequences for overall homology of the entire sequence and for different local regions and applying several filters for identifying candidate human sequences. Selection criteria for such filters include preservation of loop lengths of mouse CDRs in human sequences, sequence homologies in loops and optionally, application of several explicit and derivable recognition features as determined by constructing molecular models of antibodies.

It is commonly known that transfer of CDRs from a non-human antibody to a human framework results in a reduction in binding to antigen. The reduced affinity is due to the loss in the molecular recognition between the antigen and the human adapted antibody. The underlying cause for the loss in free energy is the structural changes in the antibody surface at the altered antibody-antigen interface. This interface involves all 6 CDRs, 3 each in VL and VH and also induced structural changes in the region due to altered packing of the new VL and VH. In order to gain some of the lost affinity, several groups have mutated residues in the human frameworks to mouse residues, referred to in the literature as back mutations. The human adaptation method described in this application does not require introduction of back mutations. The retention of affinity of the human-adapted antibodies is due to the rationale used in the selection of frameworks. The framework are chosen based not only on the overall sequence identities over the entire molecule but also on the loop length and sequence identities of all 6 CDR loops, 3 each in VL and VH. Such a rationale ensures minimal perturbations in the recognition surface of the antibody and consequently the affinity of the antibody to antigen, when one moves from a non-human to a human-adapted antibody.

A combination of sequence and structure-based criteria are used in the methods of the invention. Methods of the invention include methods of extracting and analyzing sequences and structures in databases such as human immunoglobulin database at NCBI (http:_//www_ncbi_nlm_nih_gov/) and human germline immunoglobulin database (http:_//www_v-base_mrc-cpe_cam_ac_uk/) and protein structural database (http:_www_rcsb_org).

Figure 3:
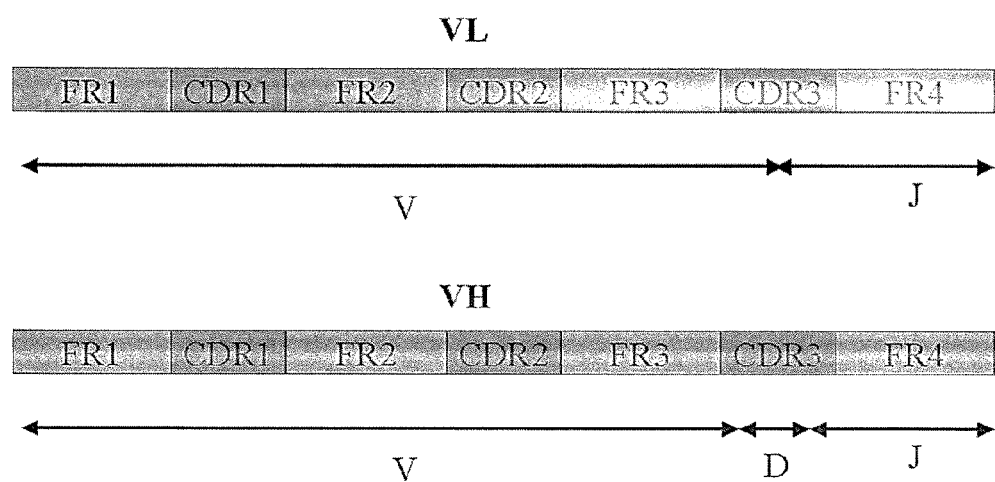
FIG. 3 illustrates antibody gene recombination for heavy and light chain variable regions.

Germline V and J gene sequences were downloaded from VBase (http:_//www_vbase_mrc-cpe_cam_ac_uk/) database. VBase is a comprehensive directory of all human germline variable region sequences compiled from over a thousand published sequences, including those in the current releases of the Genbank and EMBL data libraries. The database has been developed over several years at the MRC Centre for Protein Engineering as an extension of work on the sequencing and mapping of human antibody genes. The database contains sequences for heavy and light chain V and J genes. A framework consists of four short framework regions (FR). As seen in FIG. 3, FR1, FR2 and FR3 together with CDR1, CDR2 and a portion of CDR3 are encoded by the germline V gene fragment, while FR4 is encoded by the germline J gene fragment. For searching non-human sequence against human antibody sequences containing somatic mutations, the human immunology database from NCBI (http:_//www_ncbi_nlm_nih_gov) can be used.

There are two systems of CDR assignments for antibodies that are widely used for sequence delineation. The Kabat CDR definition is based upon antibody sequence variability. The Chothia CDR definition is based on three-dimensional structures of antibodies and topologies of the CDR loops. In the method of the invention, a consensus of the two methods is used to define CDRs. In the case of the light chain CDRs, the Kabat definition is used. In the case of heavy chain CDR3, both Kabat and Chothia's definition are identical and either can be used. In the case of heavy chain CDR1, the Kabat definition starts eight residues after the first cysteine, whereas Chothia's definition starts three residues after this cysteine. In this case, the Chothia definition was used. Kabat definition uses an ending pattern for CDR1 which is a W followed by a hydrophobic amino acid such as V, I or A. Chothia's definition ends 4 residues earlier for this CDR. In this case, the Kabat pattern for the CDR2 end definition was used. In the case of VH-CDR2, Kabat's definition was used. However, in most antibody structures, this sequence-based definition assigns a portion of FR3 as belonging to CDR2. Thus, a shorter version of this CDR, which ends 7 residues earlier on the C-terminal region of this CDR could also be used. In some instances, a molecular model of the mouse variable region is constructed. The model is used as a guide for CDR loop assignments. Table 1 shows exemplary CDR assignments that can be used in the method of the invention.

TABLE 1

| CDR loops | Start definition | End definition |
|---|---|---|
| VL-CDR1 | Kabat | Kabat |
| VL-CDR2 | Kabat/Chothia | Kabat |
| VL-CDR3 | Kabat | Kabat |
| VH-CDR1 | Chothia | Kabat |
| VH-CDR2 | Kabat | Kabat, Kabat-7 |
| VH-CDR3 | Kabat/Chothia | Kabat/Chothia |

The above definitions of CDRs are used for identifying human sequences that have the best overall similarity and, also maximum length compatibilities and sequence similarities in the CDRs loops to the non-human sequence.

Figure 2:
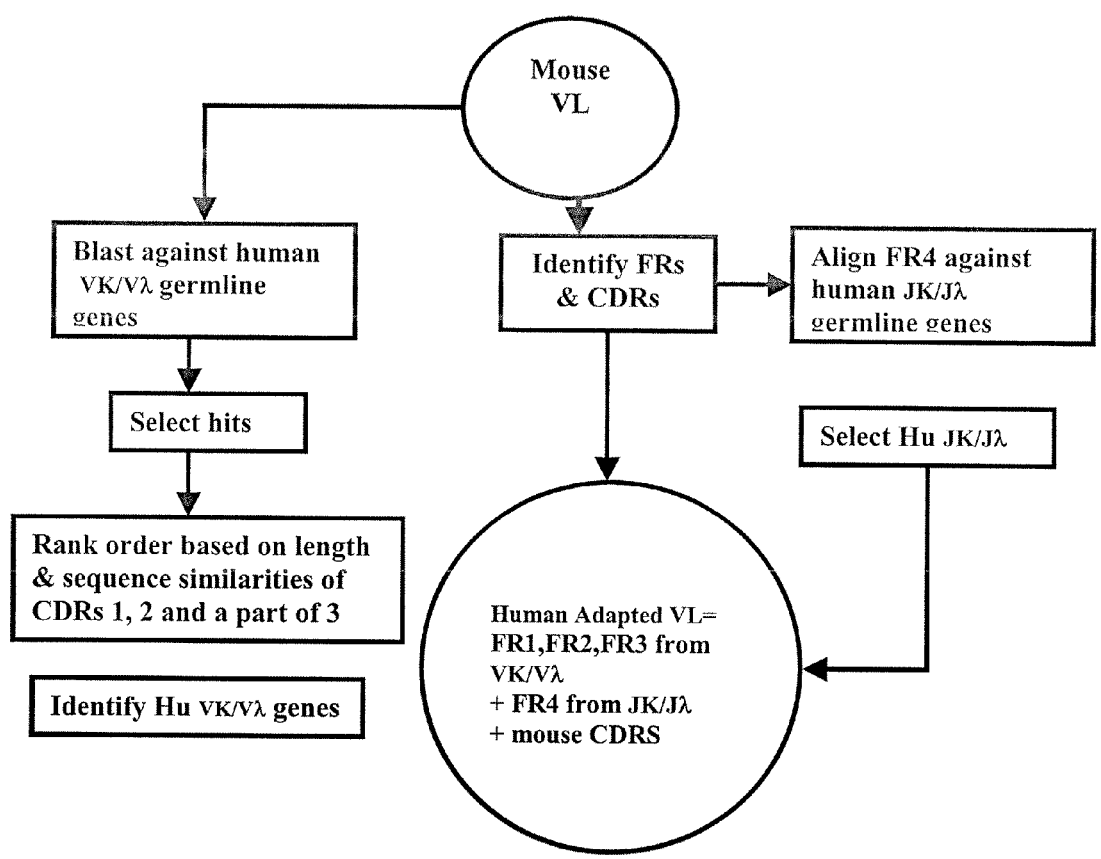
FIG. 2 shows a flowchart for the human adaptation of a mouse antibody light chain using a database of human germline light chains.

Flow charts of the method of the invention for selection of human germline heavy and light chains are shown in FIGS. 1 and 2.

The method of the invention provides for selection of human sequences that satisfy the following criteria:

1. The human sequences have significant identity with mouse sequence over the entire length of the molecule, covering all 4 frameworks and 3 CDRs.
2. The human sequences have maximum preservation of lengths of CDRs 1, 2 and 3, i.e., an alignment of human and mouse sequences has the least number of deletions and insertions in the 3 CDRs.
3. Among sequences in the human database, selected sequences have significant homology with the mouse sequence in CDRs 1, 2 and 3.

In one embodiment of the method for selecting human antibody sequences for use in making human-adapted antibody molecules, the steps comprise the following:

a. obtaining a peptide sequence for a non-human antibody variable region—typically the non-human antibody is from a rodent such as a mouse or rat. Peptide sequence information can be deduced from the nucleotide sequences of the non-human antibody variable region genes. These genes can be isolated, cloned and sequenced by techniques well known to those skilled in the art.

b. Delineating the CDRs and FRs of the non-human antibody variable region peptide sequence.

c. Providing a library of human germline antibody gene peptide sequences comprising VH, Vκ, Vλ, JH, Jκ and Jλ gene sub-libraries.

d. Selecting a subset of peptide sequences from the human germline gene library that have maximum CDR and FR similarities to the non-human antibody—non-human sequences are searched for similarity against the germ line gene database over the entire length using the BLAST program (Altschul et al., *J. Mol. Biol.* 215:403-410 (1990)) and top candidates with the best BLAST scores are selected. This step is carried out for the heavy and light chains. Non-human heavy chain is searched against human germline VH genes; non-human light chain is searched against human germline Vκ and Vλ gene sub-libraries.

e. Selecting a subset of the human antibody heavy chain sequences selected in step d based on comparison of length compatibilities of CDR1 and CDR2 loops with the non-human antibody, and sequence similarities of CDR1 and CDR2 loops with the non-human antibody—a composite score is used to assess the above two criteria. A standard mutation matrix, such as the BLOSUM 62 substitution matrix (Henikoff and Henikoff, *Proc. Natl. Acad. Sci. USA* 89: 10915-10919 (1992)) is used for scoring alignments of the CDR regions of non-human and human sequences and a large penalty applied if there is an insertion and/or deletion in the CDR loops. The process has been automated using Pipeline Pilot™ protocols (a modular software development environment available from Accelrys, Inc., San Diego, Calif.). Optionally, a user can review the scores and sequence alignments and choose a set of human germline genes to use for FRs 1, 2 and 3.

f. Selecting a subset of the human antibody light chain sequences selected in step d based on comparison of length compatibilities of CDR1, CDR2 and a portion of CDR3 loops with the non-human antibody and sequence similarities of CDR1, CDR2 and a portion of CDR3 loops with the non-human antibody—a composite score is used to assess the above two criteria as discussed above in step e.g.

g. Selecting a subset of heavy chain J gene peptide sequences from the human germ-line JH gene sub-library based on sequence similarities between framework 4 of the non-human antibody and JH gene regions h. Selecting a subset of J gene peptide sequences for the light chain from the human germ-line Jκ and Jλ gene sub-libraries based on sequence similarities between framework 4 of the non-human antibody and Jκ and Jλ gene regions i. Combining a selection of FR 1, 2 and 3 from step e and a selection of FR4 from step g for human heavy chains to select human antibody heavy chain sequences for use in making human-adapted antibodies.

j. Combining a selection of FR 1 2 and 3 from step f and a selection of FR4 from step h for human light chains to select human antibody light chain sequences for use in making human-adapted antibodies.

The entire process has been automated using Pipeline Pilot™ scripts in a visual workflow environment. The user can apply certain user-defined criteria to the process such as the display of scores, corresponding alignments and names of germline genes or setting the number of output sequences.

The method of the invention can be used with human antibody germline gene databases or human antibody gene databases containing somatic mutations. In the case of using a human antibody gene database with somatic mutations, steps e) and f) involve length compatibilities and sequence similarities of all three CDRs and there is no need for steps g) and h). The variable light and heavy chain sequences obtained can be used for generating a Fab or several Fabs. By combining these Fabs with appropriate constant regions, one can obtain full-length monoclonal antibody sequences.

Figure 4:
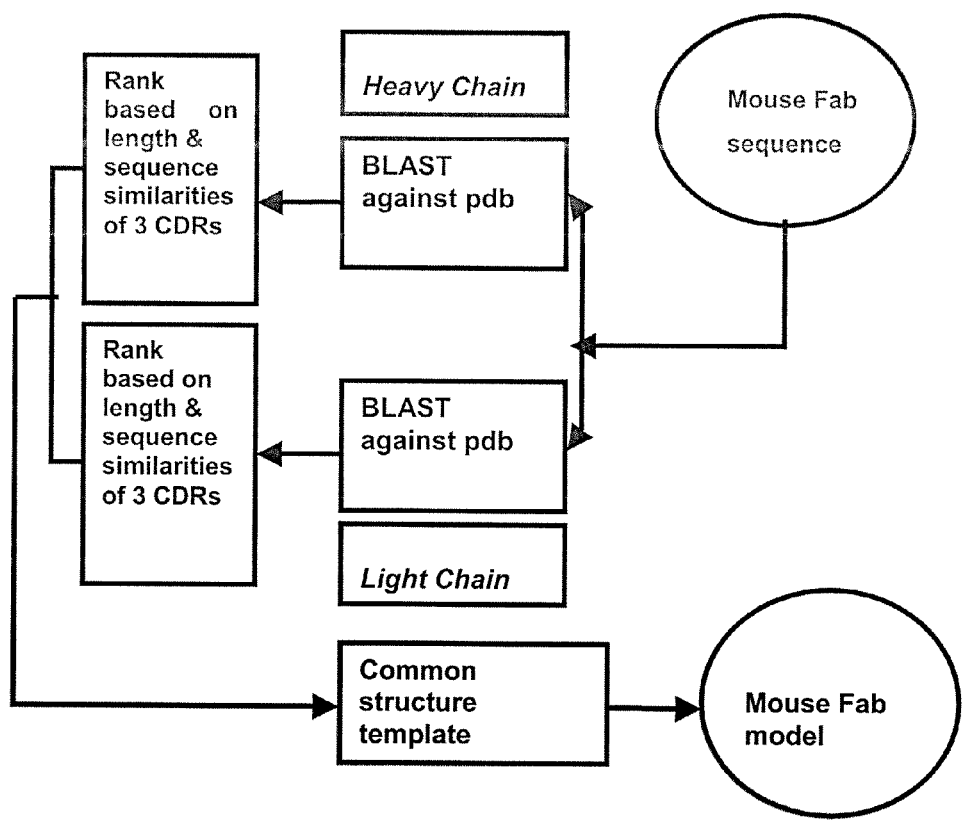
FIG. 4 shows an antibody modeling algorithm flowchart. If a common structural template is not available, the chains are individually modeled and combined. pdb designates the Protein Data Bank database (http:_//www_pdb_org).

In addition to sequence based methods, structure/model based approaches can also be used. Molecular models of the non-human antibody V regions are highly useful for deriving structural features of the molecule and hence for engineering to improve properties of interest. Quality of the model is very important and in the case of models based on a homologous structural template, reliable alignment of the target and template sequences is highly critical. See, e.g., Sali and Blundell, J. Mol. Biol. 234:779 (1993). The flowchart shown in FIG. 4 is used for selecting a structural template for modeling. The figure demonstrates that a template is chosen based on overall homology of the full sequence of VL or VH including all 4 frameworks and all 3 CDRS and then ranking the top hits based on loop length and also sequence similarity of the 3 CDRS.

The use of molecular models in combination with sequence comparisons is a useful option since sequence-based methods, by themselves, may not capture functional properties that are most often due to 3-dimensional features involving spatially adjacent residues that are separated in sequence. Sequence-based Kabat classification assigns part of framework in the antibody structure as belonging to CDR. Molecular models are used to correctly delineate framework and CDR regions and thus correct the sequence-based assignments. A combination of structural modeling and sequence analyses methods used here are useful for the selection of human frameworks and also for affinity maturing a human-adapted antibody.

The present invention provides a novel antibody human adaptation method. The method uses human germline V and J genes as a source of acceptor FW sequences, ranks all the acceptor molecules based upon FW similarities and other criteria between non-human antibody and human germline sequences, and generates a library of representative human adapted antibodies.

The algorithm defined above can be modified to change the size of FW library so as to match wet-lab screening capacity. For rodent antibody heavy and light chains, the corresponding FW libraries will be generated respectively, and all the human-adapted heavy and light chains will be combined for screening. Thus, the overall FW library strategy algorithm of the invention increases the likelihood of finding favorable pairs of human heavy and light chains with optimal interchain interactions that are likely important for affinity retention.

After the selection of favorable pairs of human heavy and light chain frameworks by the methods of the invention, a human adapted new molecule can be constructed that includes each of the CDR regions from the non-human variable region and framework regions from at least one member of the human heavy and light chain representative frameworks selected, wherein the new molecule is a human-adapted antibody or antibody fragment that binds the same antigen as that bound by the non-human antibody. Recombinant DNA techniques well known to those skilled in the art can be used to construct the human adapted molecules. The new molecules can then be selected by screening each molecule for binding affinity to antigen and selecting the optimal human-adapted antibody or antibody fragment.

The method of the invention provides a number of advantages over current human adaptation techniques. For example, in contrast to all other structure-based strategies, such as SDR-grafting, the method of the invention does not require detailed antibody or antigen-antibody complex structure information. Another advantage of the method of the invention is that it can provide several comparable, yet distinct humanized antibodies for the same CDR donor. This is especially useful for therapeutic antibody development, enabling researchers to select a lead candidate and have one or more follow-on or backup candidates.

Another related advantage of the method of the invention is that these comparable candidates, with their distinct sequences, may have different chemical, physiological, and pharmaceutical properties. This can be utilized in other aspects of therapeutic antibody improvement. For example, the CDRs of antibody with low solubility can be fitted to a human framework library, and a good binder with improved solubility may be selected from the resulting antibodies.

The present invention will now be described with reference to the following specific, non-limiting examples.

EXAMPLE 1

Human Adaptation of a Chimeric Monoclonal Antibody

Infliximab is a chimeric IgGκ monoclonal antibody with an approximate weight of 149 kDa. Infliximab binds specifically to human tumor necrosis factor alpha ($TNF_\alpha$) and is composed of human constant and murine variable regions (See FIGS. 16A & 16B of U.S. Pat. No. 5,656,272 for infliximab amino acid sequences (cA2)) and is sold under the tradename REMICADE®. Infliximab has a heavy chain variable region of 119 amino acids (SEQ ID NO: 1) and light chain variable region of 107 amino acids (SEQ ID NO: 2).

The method of the invention was applied to the infliximab heavy and light chain variable region sequences to select human germline VH and VL. The selected VH region is identical to human germline sequence VH3 3-72 and JH4. It is compared to infliximab framework regions in FIG. 5. The framework portion of the selected VL region, shown in FIG. 6, is identical to the human germline sequence VK1 A10 and JK3. The selected VH region sequence was combined with a human constant chain IgGκ H, CAA75030 (with A236V substitution). The selected VL region sequence combined with a human constant chain IgGκ, CAA09181.

Figure 7:
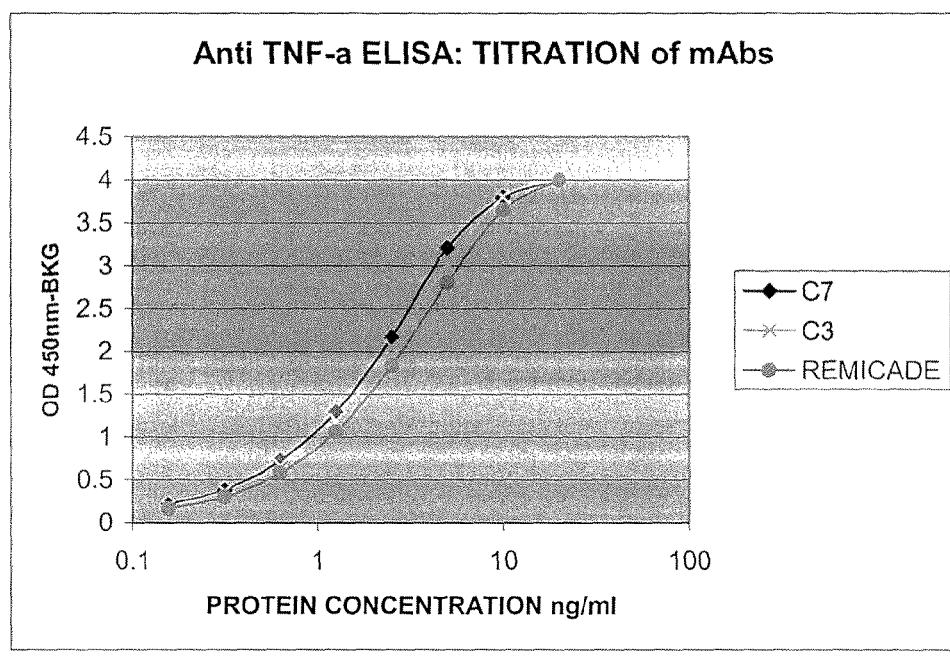
FIG. 7 shows ELISA binding titration curves for full-length human-adapted C7, infliximab synthesized in-house (C3) and commercial REMICADE® brand of infliximab.

Antibodies were assessed for binding to human $TNF_\alpha$ using an ELISA format. Briefly, human $TNF_\alpha$ was coated into the wells of a 96 well plate and candidate mAbs were incubated at various concentrations (20 to 0.2 ng/ml) and bound antibody was detected with HRP-labeled anti-human kappa light chain IgG (Jackson, ImmunoResearch, West Grove, Pa.). ELISA titration curve for the full-length clone (designated C7) is shown in FIG. 7 and indicated comparability to full-length synthetic infliximab (C3) and REMICADE®.

Binding measurements of $TNF_\alpha$ binding to C7 and REMICADE by BIACOR (3 pairs of experiments) are shown in Table 2 and also demonstrate comparability of the two antibodies.

TABLE 2

| Antibody | $k_{ass}$ (1/Ms) | $k_{diss}$ (1/s) | calc. $K_D$ (pM) |
|---|---|---|---|
| REMICADE ® | $5.47 \pm 1.37 \times 10^5$ | $9.68 \pm 5.64 \times 10^{-5}$ | 170 |
| Structure Based Human Adapted C7 | $8.03 \pm 0.93 \times 10^5$ | $5.63 \pm 0.94 \times 10^{-5}$ | 70 |

EXAMPLE 2

Human Adaptation of an Murine Monoclonal Antibody

The method of the invention was applied to a murine neutralizing Respiratory Syncytial Virus (RSV) F protein antibody designated anti-RSV 101F to select human germline VH and VL to construct the human-adapted anti-RSV antibody B21M. 101F antibody has a heavy chain variable region of 120 amino acids (SEQ ID NO: 3) and light chain variable region of 112 amino acids (SEQ ID NO: 4).

The framework of the selected VH region is identical to human germline sequence VB__2-05 and JH4. It is compared to the mouse anti-RSV F101 framework regions in FIG. 8. The selected VH region sequence was combined with a human constant chain P01857-IgG 1 (with V234A substitution). The framework of the selected VL region is identical to human germline sequence VB_B3 and JK1. It is compared to the mouse anti-RSV F101 framework regions in FIG. 9. The selected VL region sequence was combined with a human constant chain P01834-IgG k (with S227L substitution).

Figure 10:
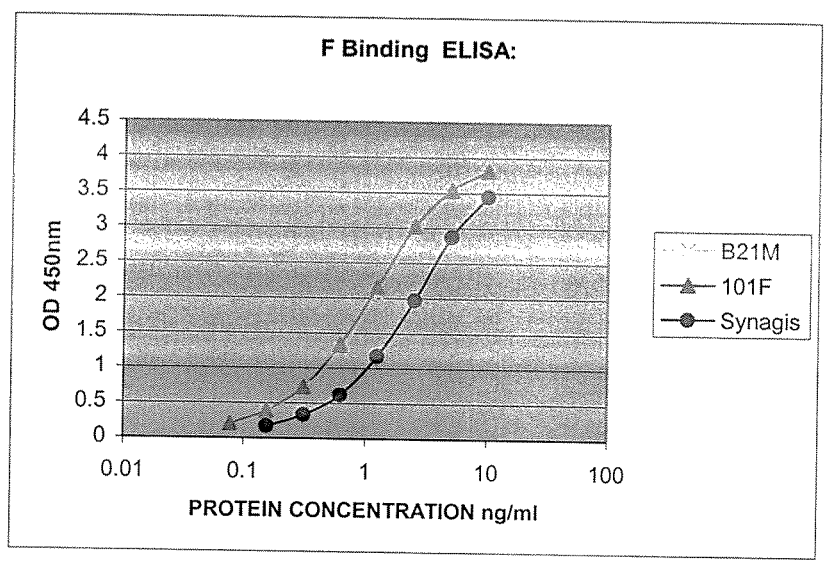
FIG. 10 shows F protein binding ELISA for chimeric anti-RSV F101 antibody, SYNAGIS® brand of pavilizumab and human-adapted B21M.
Figure 11:
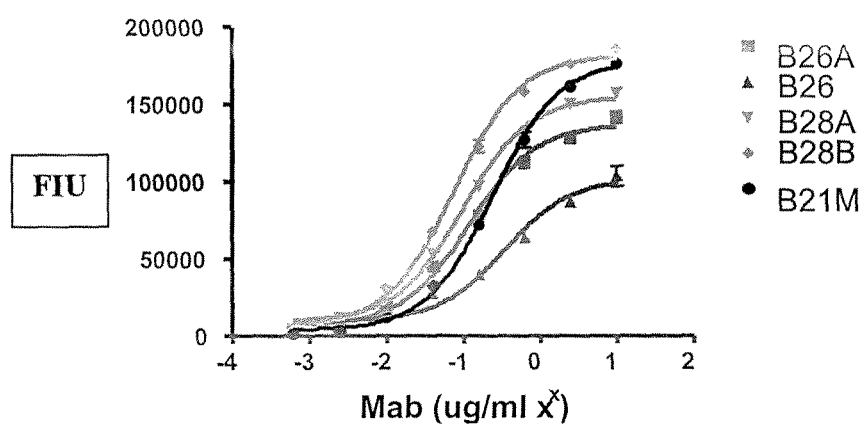
FIG. 11 shows comparison of F protein binding ELISA of the five human-adapted molecules B26A, B26, B28A, B28B and B21M.

The antibodies were assessed for binding to the extracellular domain of recombinantly expressed RSV F protein using an ELISA format. Briefly, the human RSV F protein was coated into the wells of a 96-well plate and candidate mAbs were incubated at various concentrations (10 to 0.2 ng/ml) and bound antibody was detected with HRP labeled anti human kappa light chain antibody (Jackson, ImmunoResearch, West Grove, Pa.). ELISA titration curve for the human-adapted full-length B21M clone is shown along with that for 101F antibody and the commercial product SYNAGIS® brand of pavilizumab in FIG. 10. The human-adapted B21M indicated comparability to the mouse 101F antibody and SYNAGIS®. Binding measurements as measured by BIACOR for RSV F protein binding are shown in Table 3 and also demonstrate comparability of the two antibodies. B21M also exhibits virus neutralization comparable to chimeric anti-101F antibody and SYNAGIS® (see Table 3).

TABLE 3

Surface Plasmon resonance data and virus neutralization data for B21M, Syangis and Numax

| | Synagis ® | Numax ™** | B21M |
|---|---|---|---|
| KD (nM) (Biacore) | 0.4 (+/−0.007) | 0.24 (+/−0.09) | 1.7 (+/−0.1) |
| Kon | $8.7 \times 10^5$ | $5.2 \times 10^5$ | $9.2 \times 10^5$ |
| Koff | $3.5 \times 10^{-4}$ | $1.2 \times 10^{-4}$ | $16 \times 10^{-4}$ |
| $IC_{50}$ for virus neutralization (ng/ml) | 104.0 ± 0.01 (n = 103) | 20.5 ± 0.01 (N = 3) | 13.9 ± 0.01 (n = 103) |

In order to test the validity of the method four additional light chains that were selected as top hits in the human adaptation method were used to construct human-adapted anti-RSV antibodies. The four frameworks are identical to human sequences VB_A17, VB_A10, gi:20150128 and VB_A3. The first two sequences and the fourth sequence are from human germline database and the third is a HuIg sequence. These four VLs in combination with the above VH are referred to as B21M, B26A, B26B, B28A and B28B. All of these four molecules have binding profiles similar to B21M (see FIG. 11).

The present invention now being fully described, it will be apparent to one of ordinary skill in the art that many changes and modifications can be made thereto without departing from the spirit or scope of the appended claims.

The invention claimed is:

1. A method of making human-adapted antibodies comprising selecting a human framework based on overall similarity to a non-human antibody variable region comprising the steps of:
   a) obtaining a polypeptide sequence of a non-human antibody variable region;
   b) delineating complementarity determining regions 1, 2, and 3 (CDR1, CDR2, and CDR3) and framework regions 1, 2, 3, and 4 (FR1, FR2, FR3 and FR4) in the polypeptide sequence of the non-human antibody variable region;
   c) providing a library of polypeptide sequences encoded by human variable region (V) and joining region (J) germline genes;
   d) selecting a first subset of polypeptide sequences encoded by the human V germline genes from the library of polypeptide sequences provided in step b that have maximum similarities to over the entire length of the polypeptide sequence of the non-human antibody variable region;
   e) selecting from the first subset of polypeptide sequences those polypeptide sequences that are most similar at CDR1 and CDR2 based on CDR1 and CDR2 amino acid sequence and length when compared to the non-human antibody variable region when the polypeptide sequence selected in step c is a polypeptide sequence encoding a heavy chain variable region, and those polypeptide sequences that are most similar at CDR1, CDR2, and CDR3 based on CDR1, CDR2, and CDR3 amino acid sequence and length when the polypeptide sequence identified in step c is a polypeptide sequence encoding a light chain variable region;
   f) selecting a second subset of polypeptide sequences encoded by the human J germline genes from the library of polypeptide sequences provided in step b that have maximum similarities to the polypeptide sequence encoded by a framework region 4 (FR4) of the non-human antibody variable region;
   g) generating polypeptide sequences of human antibody variable regions that show maximum homology to the non-human antibody variable region by joining the first subset of polypeptide sequences obtained in step e with the second subset of polypeptide sequences obtained in step f;
   h) transferring CDRs of the non-human antibody variable region into the polypeptide sequences of human antibody variable regions generated in step g to form human-adapted antibody variable regions; and
   i) expressing the human-adapted antibody variable regions to make the human-adapted antibodies.

2. The method of claim 1, wherein the variable region is a heavy chain variable region or a light chain variable region.

3. The method of claim 1, wherein the human antibody germline genes are selected from VH, Vκ, Vλ, JH, Jκ, or Jλ sequences.

4. The method of claim 1, wherein the human-adapted antibody is of IgG1, IgG2, IgG3, IgG4, IgM, IgD, IgE, or IgA type.

* * * * *